United States Patent [19]

Cartwright et al.

[11] 4,052,993
[45] Oct. 11, 1977

[54] CINNAMIC DERIVATIVES AS TOBACCO ADDITIVES

[75] Inventors: William F. Cartwright, Manchester, Conn.; Richard E. Means; Andrew G. Kallianos, both of Durham, N.C.

[73] Assignee: Liggett & Myers Incorporated, Durham, N.C.

[21] Appl. No.: 640,817

[22] Filed: Dec. 15, 1975

Related U.S. Application Data

[62] Division of Ser. No. 486,841, July 9, 1974, Pat. No. 3,943,943.

[51] Int. Cl.$^2$ .............................................. A24B 3/12
[52] U.S. Cl. .................................... 131/9; 131/17 R; 131/144
[58] Field of Search .................. 131/17 R, , 2, 144; 426/356–357, 358

[56] References Cited

PUBLICATIONS

Fenarali's Handbook of Flavor Ingredients, Weast, Robert-Ed., 1971, The Chemical Rubber Co., Publishers, pp. 332–336.
"Tobacco Flavoring for Smoking Products," (text) by Leffingwell et al. pp. 16 & 19 cited, published by R. J. Reynolds Tobacco Co., 1972, Winston Salem, N.C.

Primary Examiner—Robert W. Michell
Assistant Examiner—V. Millin
Attorney, Agent, or Firm—Michael L. Hendershot; J. Bowen Ross, Jr.

[57] ABSTRACT

Cinnamic derivatives, especially the methyl or ethyl ethers of cinnamyl alcohol, para-methoxycinnamyl alcohol, and para-ethoxycinnamyl alcohol, are added to tobacco to improve the flavor and aroma of the tobacco and tobacco smoke.

18 Claims, No Drawings

CINNAMIC DERIVATIVES AS TOBACCO ADDITIVES

This is a division of application, Ser. No. 486,841, filed July 9, 1974 now U.S. Pat. No. 3,943,943.

This invention is concerned with additives for tobacco. More particularly, this invention is concerned with the use of certain cinnamic derivatives as additives to improve the flavor and aroma of tobacco and tobacco smoke.

BRIEF SUMMARY OF THE INVENTION

The tobacco art contains numerous examples of the importance to the consumer of the flavor and aroma characteristics of tobacco and tobacco smoke. This has been achieved through the blending of different grades of tobacco as well as through the use of additives to the tobacco.

It is an object of this invention to provide a new class of tobacco additives for enhancing the flavor and aroma of tobacco and tobacco smoke.

It is a further object of this invention to provide a class of tobacco additives which can be employed to improve the characteristics of flavor and aroma deficient tobaccos, including reconstituted and synthetic tobaccos.

Still another object of this invention is the provision of tobacco additives which improve the flavor of smoke in charcoal filter cigarettes.

These and other objects of this invention are achieved by incorporating in tobacco a small but effective amount of a cinnamic derivative as hereinafter defined.

DETAILED DESCRIPTION

The cinnamic derivatives of the present invention may be represented by the formula:

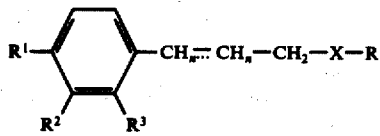

wherein X is oxygen or sulfur; $n$ is 1 or 2; the dotted line indicates the optional presence of an olefinic double bond depending on the value of $n$; R is hydrogen, lower alkyl, or lower acyl; each of $R_1$, $R_2$, and $R_3$, when taken separately, is hydrogen, lower alkyl, hydroxy, lower alkoxy, or lower acyl; and $R_1$ and $R_2$, when taken together, form a fused ring, usually containing heteroatoms, of from 5 to 6 members.

By the terms of "alkyl" and "alkoxy" are meant both straight and branched chain alkyl and alkoxy groups, such as methyl, ethyl, propyl, isopropyl, butyl, tert-butyl, the corresponding alkoxy groups and the like. Lower alkyl and lower alkoxy includes alkyl and alkoxy groups of from 1 to about 6 carbons, with those of from 1 to about 3 carbons being particularly preferred. Methyl and ethyl are most preferred alkyl groups and methoxy and ethoxy and most preferred alkoxy groups.

By the term "acyl" is meant the residue of an aliphatic acid which may be straight or branched chain. Lower acyl encompasses acyl groups of 1 to 6 carbons, preferably 2 to 3 carbons, such as acetyl.

The divalent radical formed by $R_1$ and $R_2$ can be a hydrocarbon radical which may be saturated or unsaturated. In the latter case, it may form a fused aromatic ring of 5 to 6 ring members, which may contain 1 to 2 heteroatoms such as oxygen or nitrogen. Preferred divalent radicals are alkylene, alkyleneoxy and alkylenedioxy of from 3 to 4 atoms in the chain.

Preferred compounds are those having no more than one substituent on the aromatic nucleus, with those having no substituents or a para-alkoxy substituent being especially preferred. This invention contemplates the use of both the cis-and trans-isomers of the cinnamic derivatives. In most cases the trans-isomer is the most stable isomer.

Useful embodiments of this invention include cinnamyl alcohol, cinnamyl methyl ether, cinnamyl ethyl ethyl, and cinnamyl methyl sulfide amoing others. Mono-substituted derivatives include o- and p-methoxycinnamyl alcohol, their esters and ethers such as the methyl and ethyl p-methoxycinnamyl ethers and the corresponding thioethers. Also within this group are the p-ethoxycinnamyl alcohol and p-ethoxycinnamyl-methyl ether. Such substituted compounds as 3,4-methylenedioxycinnamyl and coniferyl derivatives also fall within the scope of this invention. Examples of these compounds would be 3,4-methylene-dioxycinnamyl alcohol and its esters and ethers such as methyl 3,4-methylenedioxycinnamyl ether. The coniferyl series includes coniferyl alcohol (4-hydroxy-3-methoxycinnamic alcohol) and its esters and ethers such as methyl 4-hydroxy-3-methoxycinnamyl ether. The corresponding sulfur compounds are also applicable. Lastly, the dihydro-analogs of the foregoing cinnamyl compounds, e.g. p-methoxydihydrocinnamyl methyl ether, can be employed. It must be appreciated that the naming of specific compounds herein in no way limits the scope of this invention, and additional compounds are readily apparent to those versed in the art of organic synthesis.

A particularly preferred class of compounds are those of the formula:

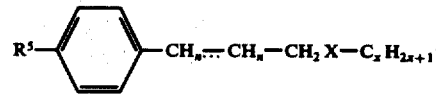

wherein X and $n$ are as defined above; $x$ has a value of from 0 to 2, inclusive, and $R_5$ is hydrogen, alkyl of 1 to 2 carbons, inclusive, or alkoxy of 1 to 2 carbons, inclusive.

The cinnamic derivatives are either commercially available or can be obtained from commercially-available compounds. For example, cinnamyl alcohol and certain of its derivatives are available commercially, and they can be converted to the corresponding esters and ethers by conventional procedures, e.g., etherification with an alkyl halide or esterification with an acyl halide. They can be converted to their thioethers by reaction with thionylchloride to produce a cinnamyl chloride, followed by reaction of the cinnamyl chloride with a sodium thioalkylate, e.g., sodium thiomethylate. If the cinnamyl alcohol is not readily available, it can be synthesized from the corresponding acid by a two-step procedure in which the acid is esterified and the resulting ester is reduced with lithium aluminum hydride.

The cinnamyl compounds are employed as additives to tobacco, especially cigarette tobacco, to modify its flavor. The specific amount employed will vary with the compound employed and the effect desired. For example, methyl p-methoxycinnamyl ether is useful in amounts of up to about 50 ppm, but at higher amounts it tends to adversely affect the flavor of the tobacco smoke. Methyl cinnamyl ether, on the other hand, can be employed in amounts exceeding 50 ppm. In general, then, the small but effective amount of cinnamyl derivative can be from 0.1 to about 1000 ppm, and is preferably from about 10 to 100 ppm.

The cinnamyl derivatives are admixed with tobacco in any convenient fashion, typically in aqueous ethanolic solution. They can be employed to modify the flavor and aroma characteristics of natural, reconstituted and synthetic tobaccos as well as blends thereof. They are of particular utility in cigarette tobaccos, and the alkyl cinnamyl ethers, especially the ethers of cinnamyl alcohol and p-alkoxycinnamyl alcohol, such as p-methoxycinnamyl alcohol, are of especial utility in tobaccos of charcoal-filter cigarettes. They substantially reduce the "charcoal effects" noted in such cigarettes.

Certain cinnamic derivatives have been employed in tobaccos before. For example, German Pat. No. 1,028,029 discloses the use of cinnamaldehyde as a tobacco preservative which does not adversely affect the taste or aroma of tobacco. There is no disclosure, however, that cinnamaldehyde can improve the flavor and taste of tobacco. Moreover, it is employed in amounts considerably higher than are contemplated by this invention. Thus, the patent teaches its use in amounts of from about 100 to about 10,000 parts per million.

In U.S. Pat. No. 3,111,951 the use of truxillic acid, the dimer of cinnamic acid, as well as alkyl and aryl esters of the acid, in amounts of 1000 to 10,000 parts per million is disclosed to improve tobacco flavor and aroma, notably to impart a cinnamon note to the tobacco smoke. This amount is substantially higher than the amounts contemplated by this invention.

Finally, applicant has discovered that methyl cinnamyl ether is a naturally occurring component of a highly aromatic Turkish tobacco. However, it is present in extremely small amounts, of the order of 6 micrograms per gram of the tobacco. Moreover, to applicant's knowledge, its presence was not appreciated by the art prior to this invention.

The following examples are illustrative:

EXAMPLE I

Methyl Cinnamyl Ether

Commercial cinnamyl alcohol was purified by distillation to yield a crystalline product, mp 33°. Sixty-seven (67) grams of the purified cinnamyl alcohol (0.5 mole) and 83 gm of iodomethane (0.584 mole, 15% excess) were dissolved in 300 cc of dimethoxyethane which had just been distilled from lithium aluminum hydride. This solution was placed in a 3-necked round bottomed flask equipped with a magnetic stirrer and condenser. Over a period of 30 to 40 minutes 13 gm (0.542 mole) of pure sodium hydride was added to the reaction mixture in batches. The sodium hydride was obtained by washing a 57% oil suspension (23.7 gm) with ether just prior to addition. The heat of reaction brought the solution to reflux, and 10 minutes after the last sodium hydride addition 10cc of iodomethane was added. Stirring at room temperature was continued for another 1½ to 2 hours. The solution was then filtered to remove sodium iodide and the solvent was evaporated off under reduced pressure. The residual oil was treated with ethyl ether and the precipitated sodium iodide was again removed by filtration. The ethyl ether was evaporated and the residual light yellow oil was distilled under aspirator pressure to give 62 gm (84% yield) of methyl cinnamyl ether (b.p. 105° C.): $\lambda_{max}^{CCl_4}$ 3.3–3.55 (CH, OCH$_3$), 6.68 and 14.48 (ar.), 6.88 (CH$_2$), 7.25 (CH$_3$), 8.4 (C-O), and 10.35 μ (trans CH=CH). The NMR (δ) showed absorbances at 7.1–7.5 (m,arom.), 5.9–6.9 (m, vinyl), 3.9–4.1 (d, CH$_2$) and 3.3 (s,CH$_3$) in good agreement with the assigned structure. Gas chromatographic analysis indicated a purity of at least 99%, with the methyl cinnamyl ether having a retention time (Rt) of 6.3 minutes as compared to 24.3 minutes for the starting alcohol (5% FFAP, ¼ inch × 10 feet, 200° C, 40cc He/min).

Methyl cinnamyl ether exhibits a persistent sweet cinnamon note. It was evaluated organoleptically in tobacco at levels ranging from 0 to 120 ppm (increments of 20 ppm). The preferred concentration on tobacco was established as being on the order of 50 ppm. At this level, methyl cinnamyl ether contributed somewhat more fullness to the smoke while adding a sweet note.

Methyl cinnamyl ether proved particularly advantageous when utilized in charcoal filter cigarettes. At 50 ppm, the typical "charcoal effects" of these cigarettes were reduced, the overall flavor and balance was improved, and the tobacco flavor was enhanced.

EXAMPLE II p-Methoxycinnamyl Alcohol p-Methoxycinnamic acid was dissolved in refluxing methanol containing a catalytic amount of hydrogen chloride to form methyl p-methoxycinnamate. The yield of purified ester was 85%, m.p. 88°–89° (lit. 90°; Dictionary of Organic Compounds, II, Sir Ian Heilbron, ed., p. 600 (1946)): $\lambda_{max}^{CCl_4}$ 3.32, 3.38 and 3.52 (CH$_1$–OCH$_3$), 5.81 (C=O), 6.1 and 10.15 (CH=CH, trans), 7.95 and 8.5–8.6 (ester)μ. The NMR (δ) supported the expected structure: 6.13–7.78 (series of multiples, aromatic and vinyl), 3.86 (—CO$_2$CH$_3$), and 3.78 (AR—O—CH$_3$).

The ester (65 gm, 0.34 mole) was then reduced with lithium aluminum hydride (hereinafter LAH), in benzene by the method of E. Snyder, J. Am. Chem. Soc., 88, 1464 (1964), using 900cc benzene to which 15.7 gm (0.41 mole) of LAH was added with cooling (icebath) over one hour. Stirring was continued at room temperature overnight. To obtain a filtrable aluminate complex $n$ cc of water, $n$ cc of 15% sodium hydroxide, and 3$n$ cc of water (where $n$ equals grams LAH) were added to the reduction slurry. (See V. M. Micovic, M. J. Mihailovic, J. Org. Chem. 18, 1190(1935)). The filtered solids were washed well with ether and the combined organics evaporated under reduced pressure. p-Methoxycinnamyl alcohol, crystallized from ether, was obtained in a yield of 41.2 grams (75%), mp 75°–77°: $\lambda_{max}^{CHCl_3}$ 2.77, 1.9 (—OH), 3.42 (CH), 6.05 (CH=CH), 6.22, 6.33, and 6.63 (arom.), 8.53, 9.23 and 9.68 (C-O). No unusual features were observed in the NMR (δ): 6.0–7.5 (multiplets, aromatic and vinyl), 4.3 (d, —CH$_2$—), 3.72 (s, —OCH$_3$), and 1.7 (s, —OH).

At 50 ppm, the alcohol imparted a spicy note to the smoke which is advantageous for providing the smoke with "character".

EXAMPLE III

Methyl p-Methoxycinnamyl Ether

Methyl p-methoxycinnamyl ether was obtained by treating 40 grams p-methoxycinnamyl alcohol (242 mM) in 300 cc dry dimethoxyethane, with 41 gms iodomethane (289 mM) and 6.4 gms pure sodium hydride (267 mM). After filtration of sodium iodide and removal of solvent, the remaining oil was distilled to yield 38.2 gms (88%) of chromatographically pure ether: b.p. (Vacuum) 104.5°–106° C.: $\lambda_{max}^{CCl_4}$ 3.43, 3.54 (—CH, —OCH$_3$), 6.22, 6.62 and 10.35 (CH=CH, trans), 8.92 and 9.62 (C-O) $\mu$. The NMR ($\delta$) was uneventful: 7.04 (AB mult., arom.), 6.24 (m, vinyl), 4.0 (d, —CH$_2$—), 3.78 (Ar—O—CH$_3$), and 3.30 (—C-O-CH$_3$). GC analysis gave only one peak (Rt = 25.2 minutes) on a 5% FFAP, ⅛ inch × 10 feet column (200° C., 35cc He/min.).

The ether is of particular interest because it was considered by several people knowledgeable in the art of flavoring to possess a very pleasant sweet-caramel, heavy-bodied aroma complex. A trained panel evaluated the ether on tobacco at levels of 25, 50, 100 and 200 ppm. Cigarettes treated with 50 ppm of the ether were felt to deliver a sweeter, smoother smoke with an attendant increase in both fullness and depth. The same level in charcoal filter cigarettes was also advantageous, decreasing the typical "charcoal effects" and adding some sweetness and balance to the smoke flavor.

EXAMPLE IV

Methyl Cinnamyl Sulfide

Cinnamyl alcohol was purified in the manner of Example I and subsequently reacted with thionyl chloride to yield the corresponding chloride: $\lambda_{max}^{CCl_4}$ 8.0 and 14.39 (aromatic), 10.37 CH=CH, trans) and 14.78 (C-Cl)$\mu$. Subsequent reaction of the chloride with sodium thiomethylate gave methyl cinnamyl sufide in moderate yield after distillation (vacuum, 78° C). The infrared spectrum of the product was in agreement with the proposed structure and GC analysis indicated a purity of at least 99%: $\lambda_{max}^{CCl_4}$ 6.67, 6.87, 7.70, 8.90, 9.3, 9.7, 10.4, and 14.4 $\mu$.

Methyl cinnamyl sulfide was evaluated at levels of 1, 10, 25 and 100 ppm. Only the lowest level proved advantageous in that candy-like and chocolate notes were contributed to the smoke.

EXAMPLE V

Ethyl Cinnamyl Ether

Reaction of cinnamyl alcohol with ethyl iodide was carried out in the same manner as described in Example I. The analytical data supported the assigned structure and GC analysis indicated a purity of 99: +% $\lambda_{max}^{CCl_4}$ 6.66, 6.87, 7.25, 8.75–9.1, 10.35 and 14.45 $\mu$.

The flavor notes and utility of the ethyl ether are much the same as described for the methyl ether of Example I. However, this compound possesses the added advantages that it provides a somewhat smoother smoke as well as range of application extending to higher levels than appropriate for the methyl ether.

EXAMPLE VI

Ethyl p-Methoxycinnamyl Ether

Reaction of p-methoxycinnamyl alcohol with ethyl iodide in the same manner as described under Example III gave an 80% yield of ethyl p-methoxycinnamyl ether after molecular distillation (vacuum, 105° C): $\lambda_{max}^{CCl_4}$ 6.1, 6.6, 6.75, 8.0, 8.55, 8.92, 9.55, 10.15, 10.8, and 12.05 $\mu$.

The same advantages accrue to the ethyl ether as the methyl ether given in Example III with the added advantages of providing a somewhat smoother smoke and effective addition levels higher than those appropriate for the corresponding methyl ether.

EXAMPLE VII p-Methoxydihydrocinnamyl Methyl Ether

The ether described in Example III was hydrogenated in a Parr apparatus using 10% Pd-on-C in absolute ethanol. The compound was purified by molecular distillation and gave a single peak on GC analysis: $\lambda_{max}^{CCl_4}$ 6.18, 6.6, 6.8, 7.67, 8.02, 8.49, 8.91 and 9.58 $\mu$. Analytical data (MS and NMR) agreed with the assigned structure.

Organoleptic evaluation demonstrated that the product provided a pleasing sweet note when applied at a level of 25 ppm.

EXAMPLE VIII p-Ethoxycinnamyl Methyl Ether p-Hydroxycinnamic acid (Aldrich, mp 214° C, dec.) was esterified routinely in methanolic hydrogen chloride to give methyl p-hydroxycinnamate, mp 144° C (lit., 137° C): 1 $\lambda_{max}^{CCl_4}$ 3.04, 5.86, 6.11, 6.6, 6.94, 7.51, 8.56, 10.15 and 12.0 $\mu$.

We will refer to Heilbron, "Dictionary of Organic Compounds", II, (1946).

This ester was treated with excess ethyl iodide in the presence of potassium carbonate in refluxing dry acetone for 48 hours. A moderate yield of methyl p-ethoxycinnamate was obtained as white crystals from methanol, mp 68°–70° C: $\lambda_{max}^{CCl_4}$ 5.8, 6.09, 6.22, 6.6, 8.0, 8.56, 9.53, 10.15, and 10.08 $\mu$. Reduction of methyl p-ethoxycinnamate in benzene with LAH gave a 50% yield, after recrystallization from methanol, of p-ethoxycinnamyl alcohol, mp 85° C: $\lambda_{max}^{CCl_4}$ 2.75, 6.2, 6.61, 6.75, 8.93, 9.2, 9.55, 9.97, 10.3, 10.85, and 11.87 $\mu$.

Alkylation of this alcohol according to conditions described in Example I, provided a 96% yield of p-ethoxycinnamyl methyl ether as a low melting (34° C) white solid ($\lambda_{max}^{CCl_4}$ 6.04, 6.2, 6.6, 6.75, 7.0, 8.06, 8.95, 9.5, 10.34, 10.8 and 11.85 $\mu$) which was pure by GC analysis (Rt =23 minutes, conditions as described in Example I). The NMR spectrum was consistent with the proposed structure: ($\delta$) 1.33 (t, CH$_3$CH$_2$—), 3.25 (s, —OCH$_3$), 3.88 (m, both —CH$_2$—) and the phenyl and vinyl protons appear as a broad multiplet in the 6.7 region.

At 50 ppm mouth effects were increased slightly giving the cigarette increased body. The smoke exhibited increased fullness and tobacco fragrance. At 20 ppm, the effects could still be detected but they were much less pronounced. This ether's utility is similar to that described under Example III but can be applied beneficially at somewhat higher levels.

What is claimed is:
1. The method of improving the flavor and aroma of tobacco and tobacco smoke which comprises adding to tobacco a flavor and aroma improving amount of a cinnamic derivative of the formula:

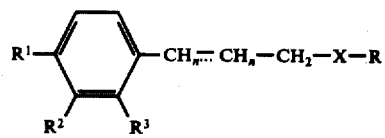

wherein X is sulfur; n is 1 or 2; the dotted line signifies the optional presence of an olefinic double bond depending upon the value of n; each of $R^1$, $R^2$, and $R^3$, when taken separately, is hydrogen, lower alkyl, hydroxy, lower alkoxy or lower acyl and $R^1$ and $R^2$, when taken together, form a divalent radical which forms a fused ring of from 5 to 6 ring members; and R is hydrogen, lower alkyl, or lower acyl.

2. The method of claim 1 wherein the amount of said derivative is in the range of from about 0.1 to about 1000 ppm.

3. The method of claim 2, wherein n is 1.

4. The method of claim 3, wherein $R^1$, $R^2$, and $R^3$ are hydrogen.

5. The method of claim 4, wherein R is hydrogen.

6. The method of claim 4, wherein R is lower alkyl.

7. The method of claim 6, wherein R is methyl.

8. The method of claim 4, wherein R is lower acyl.

9. The method of claim 3, wherein $R^2$ and $R^3$ are hydrogen.

10. The method of claim 9, wherein $R^1$ is methoxy.

11. The method of claim 10, wherein R is hydrogen.

12. The method of claim 10, wherein R is lower alkyl.

13. A tobacco composition comprising tobacco and an amount of a cinnamyl derivative sufficient to improve the flavor and aroma characteristics of the tobacco and tobacco smoke, said cinnamic derivative having the formula:

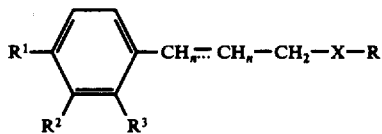

wherein X is sulfur; n is 1 or 2; the dotted line signifies the optional presence of an olefinic double bond depending upon the value of n; each of $R^1$, $R^2$, and $R^3$, when taken separately, is hydrogen, lower alkyl, hydroxy, lower alkoxy, or lower acyl; and $R^1$ and $R^2$, when taken together, form a divalent radical which forms a fused ring of from 5 to 6 members; and R is hydrogen, lower alkyl, or lower acyl.

14. The composition according to claim 13 wherein said amount is in the range of from about 0.1 to about 1000 ppm.

15. An improved charcoal filter cigarette wherein the improvement comprises a tobacco composition containing an amount of a cinnamic derivative sufficient to reduce the "charcoal effect" of said cigarette, said cinnamic derivative having the selected formula:

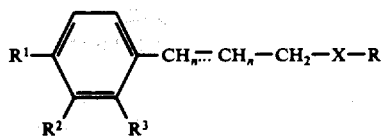

wherein X is sulfur; n is 1; each of $R^1$, $R^2$, and $R^3$, when taken separately, is hydrogen, lower alkyl, hydroxy, lower alkoxy, or lower acyl; and $R^1$ and $R^2$, when taken together, form a divalent radical which forms a fused ring of from 5 to 6 members; and R is hydrogen, lower alkyl, or lower acyl.

16. The cigarette according to claim 15 wherein said amount is in the range of from about 0.1 to about 1000 ppm.

17. A tobacco composition comprising tobacco and from about 0.1 to about 1000 ppm, based on the weight of tobacco, of a compound having the formula:

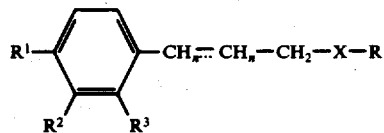

wherein X is oxygen; n is 1 or 2; the dotted line signifies the optional presence of an olefinic double bond depending on the value of n; each of $R^1$, $R^2$, and $R^3$, when taken separately, is hydrogen, lower alkyl, hydroxy, lower alkoxy, or lower acyl; and $R^1$ and $R^2$, when taken together, form a divalent radical which forms a fused ring of from 5 to 6 members; and R is lower acyl.

18. The composition of claim 17 wherein $R^1$, $R^2$ and $R^3$ are hydrogen and has a value of 1.

* * * * *